(12) United States Patent
Hernandez-Guerra et al.

(10) Patent No.: US 6,240,162 B1
(45) Date of Patent: *May 29, 2001

(54) PRECISION DOSIMETRY IN AN INTENSITY MODULATED RADIATION TREATMENT SYSTEM

(75) Inventors: Francisco M. Hernandez-Guerra, Concord; Edward Lewis Calderon, Pittsburg; Simon John Forknall, Concord; David L. Pond, Novato; Hussein Alaifai, Pleasant Hill; Randall V. Tarr, Concord, all of CA (US)

(73) Assignee: Siemens Medical Systems, Inc., Iselin, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/178,388

(22) Filed: Oct. 23, 1998

Related U.S. Application Data

(63) Continuation-in-part of application No. 09/007,304, filed on Jan. 15, 1998, now Pat. No. 6,038,284.

(51) Int. Cl.[7] ................................................. A61N 5/10
(52) U.S. Cl. ............................................. 378/65; 378/108
(58) Field of Search ................................ 328/65, 96, 97, 328/108; 250/492.1, 492.3

(56) References Cited

U.S. PATENT DOCUMENTS

| 2,920,228 | | 1/1960 | Ginzton . | |
|---|---|---|---|---|
| 3,871,360 | | 3/1975 | Van Horn et al. . | |
| 3,871,579 | * | 3/1975 | Inamura | 378/108 |
| 3,894,235 | * | 7/1975 | Franke | 378/96 |
| 3,971,945 | * | 7/1976 | Frane | 378/96 |
| 4,032,784 | * | 6/1977 | Rich | 378/108 |
| 5,148,032 | * | 9/1992 | Hernandez | 250/492.1 |
| 5,155,752 | * | 10/1992 | Kawakami | 378/97 |
| 5,400,384 | * | 3/1995 | Fernandez | 378/108 |
| 5,538,494 | | 7/1996 | Matsuda . | |
| 5,563,925 | * | 10/1996 | Hernandez | 378/150 |
| 5,663,999 | * | 9/1997 | Siochi | 378/65 |
| 5,668,847 | * | 9/1997 | Hernandez | 378/65 |
| 5,754,622 | * | 5/1998 | Hughes | 378/65 |
| 6,038,284 | * | 3/2000 | Hernandez-Guerra et al. | 378/65 |

FOREIGN PATENT DOCUMENTS

| 0 093 897 | 11/1983 | (EP) . |
|---|---|---|
| WO 98/16151 | 4/1998 | (WO) . |

* cited by examiner

Primary Examiner—David P. Porta (57) ABSTRACT

A system and method for radiation therapy delivery. Known errors are compensated for by applying an offset factor to the dose at the start of the beam cycle. According to one embodiment of the invention, a dosimetry controller is configured to provide the offset connection and sense radiation on (RAD ON) and monitor the dose rate at the beginning of the beam cycle.

17 Claims, 9 Drawing Sheets

PRECISION DOSIMETRY IN AN INTENSITY MODULATED RADIATION TREATMENT SYSTEM

CROSS REFERENCE TO RELATED APPLICATIONS

This case is continuation-in-part of application Ser. No. 09/007,304 filed Jan. 15, 1998, entitled "Precision Dosimetry in an Intensity Modulated Radiation Treatment System" now U.S. Pat. No. 6,038,284. This case is also related to commonly assigned applications Ser. No. 09/007,441, entitled "Precision Beam Control for an Intensity Modulation Treatment System" now U.S. Pat. No. 6,052,435 and Ser. No. 09/007,444, entitled "System and Method for Dose Monitoring in an Intensity Modulated Radiation Treatment System" now U.S. Pat. No. 6,108,399. All three applications were concurrently filed on Jan. 15, 1998.

BACKGROUND OF THE INVENTION

The present invention relates to a radiation emitting device, and more particularly, to a system and method for efficiently delivering radiation treatment.

DESCRIPTION OF THE RELATED ART

Radiation emitting devices are generally known and used, for instance, as radiation therapy devices for the treatment of patients. A radiation therapy device generally includes a gantry which can be swiveled around a horizontal axis of rotation in the course of a therapeutic treatment. A linear accelerator is located in the gantry for generating a high energy radiation beam for therapy. This high energy radiation beam can be an electron beam or photon (X-ray) beam. During treatment, this radiation beam is trained on one zone of a patient lying in the isocenter of the gantry rotation.

In the case of an electron beam, for example, the electron accelerator typically includes an electron gun, accelerating cavities, an exit window, and a radio frequency input. A trigger system generates modulator and injector signals and supplies them to an injector and a high voltage modulator. The modulator generates the radio-frequency pulses and the injector generates the injector pulses. The injector pulses control the quantity of the electrons that will be emitted by the electron gun. The radio frequency creates an electromagnetic field in the accelerator which accelerates the electron beam toward the exit window. The injector and the radio frequency pulses must be synchronized; otherwise, beam acceleration will not occur.

To control the radiation emitted toward an object, a beam shielding device, such as a plate arrangement or a collimator, is typically provided in the trajectory of the radiation beam between the radiation source and the object. An example of a plate arrangement is a set of four plates that can be used to define an opening for the radiation beam. A collimator is a beam shielding device which could include multiple leaves, for example, a plurality of relatively thin plates or rods, typically arranged as opposing leaf pairs. The plates themselves are formed of a relatively dense and radiation impervious material and are generally independently positionable to delimit the radiation beam.

The beam shielding device defines a field on the object to which a prescribed amount of radiation is to be delivered. The usual treatment field shape results in a three-dimensional treatment volume which includes segments of normal tissue, thereby limiting the dose that can be given to the tumor. The dose delivered to the tumor can be increased if the amount of normal tissue being irradiated is decreased and the dose delivered to the normal tissue is decreased. Avoidance of delivery of radiation to the organs surrounding and overlying the tumor determines the dosage that can be delivered to the tumor.

The delivery of radiation by a radiation therapy device is prescribed and approved by an oncologist. The prescription is a definition of, for example, a particular volume and the level of radiation permitted to be delivered to that volume. Actual operation of the radiation equipment, however, is normally done by a therapist. When the therapist administers the actual delivery of the radiation treatment as prescribed by the oncologist, the radiation-emitting device is programmed to deliver that specific treatment. When programming the treatment, the therapist has to take into account the actual radiation output and has to adjust the dose delivery based on the plate arrangement opening to achieve the prescribed radiation treatment at the desired depth in the target.

The oncologist's challenge is to determine the best number of fields and delivered intensity levels to optimize the dose volume histograms, which define a cumulative level of radiation which is to be delivered to a specified volume. To optimize dose volume histograms to the prescriptions, the three-dimensional volume is broken into cells, each cell defining a particular level of radiation to be administered. The outputs of the optimization engines are intensity maps, which are determined by varying the intensity at each "cell" in the map. The intensity maps specify a number of fields defining desired (optimized) intensity levels at each cell. The fields may be statically or dynamically modulated, such that a different accumulated dosage is received at different points in the field. Once radiation has been delivered according to the intensity map, the accumulated dosage at each cell, or dose volume histogram, should correspond to the prescription as closely as possible.

One technique used in conjunction with intensity modulation is auto-sequencing. In an auto-sequencing technique, the field segments are delivered in via a verify and record system in a rapid and fully automated manner. An important component of auto-sequencing is the ability to cycle the radiation beam on and off quickly and accurately during an intensity modulation radiation treatment.

With both single beam and auto-sequencing techniques, the ion chambers and analog and digital dosimetry circuitry can introduce delays which can cause inaccuracies in the applied radiation. These delays are not generally significant with regard to single beam cycle beam treatments, since their effect on linearity is only about 2%. However, when the treatment field is split into many segments, each with its own beam cycle, the error may be orders of magnitude greater, since the amount of the error increases with the number of segments being treated.

In addition, linearity errors between delivered and programmed dosages have been found to be particularly significant for prescribed treatments of less than 10 MUs. Such errors are in compliance with current linearity specifications since linearity is not specified below 50 MUs. However, since IMRT can require the delivery of as little as 1 MU, there is a need for an improved linearity performance below 50 MU.

Accordingly, there is a need for a method for compensating for dosimetry delays in a radiation treatment device.

SUMMARY OF THE INVENTION

These problems in the prior art are overcome in large part by a system and method for control of radiation therapy delivery according to the present invention. In particular, known delays are compensated for by applying a compensation factor to the dose at the start of the beam cycle. According to one embodiment of the invention, a dosimetry controller is configured to sense radiation on (RAD ON) and monitor the dose rate at the beginning of the beam cycle. The dosimetry controller then multiplies the dose rate by a compensation factor. Thus, for each beam cycle, the dosimetry controller resolves the magnitude of the lost dose rate data and compensates each segment accordingly.

According to one embodiment of the invention, the compensation factor is a multiplication factor. According to another embodiment, particularly useful for low dosages, the compensation factor is an offset.

BRIEF DESCRIPTION OF THE DRAWINGS

A better understanding of the present invention can be obtained when the following detailed description is considered in conjunction with the following drawings in which.

DETAILED DESCRIPTION OF THE INVENTION

SYSTEM OVERVIEW

Figure 1:
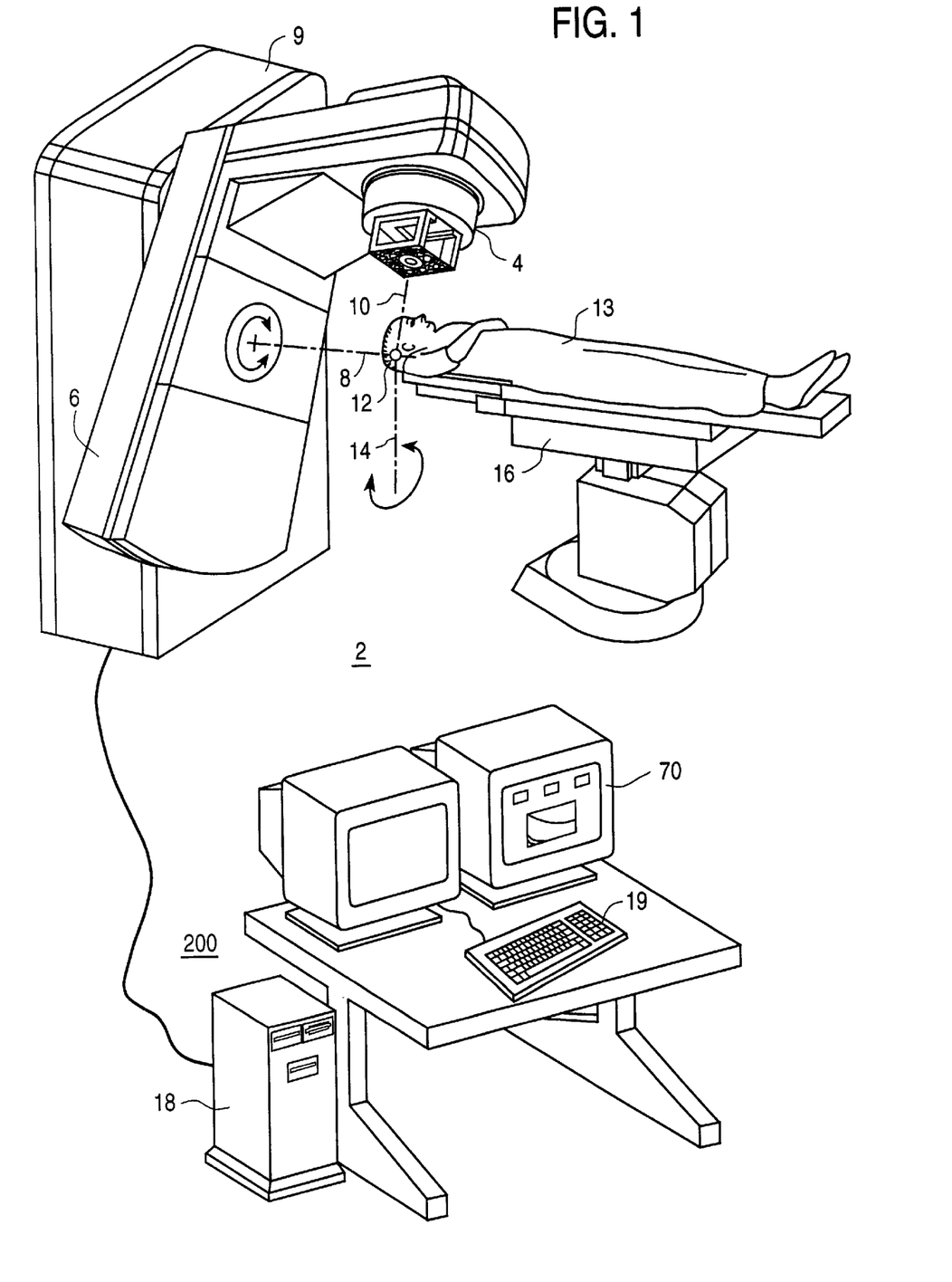
FIG. 1 is a diagram of a radiation treatment device and treatment console according to an embodiment of the present invention.

Turning now to the drawings and, with particular attention to FIG. 1, a radiation treatment apparatus embodying the present invention is shown therein and generally identified by reference numeral 2. The radiation treatment apparatus 2 is configured to vary the synchronization of the RF modulator pulse and the injector pulse, as will be discussed in greater detail below. The radiation treatment apparatus 2 includes a beam shielding device (not shown) within a treatment head 4, a control unit in a housing 9 and a treatment unit 200 according to the present invention. The radiation treatment device 2 includes a gantry 6 which can be swiveled around a horizontal axis of rotation 8 in the course of a therapeutic treatment. The treatment head 4 is fastened to projection of the gantry 6. A linear accelerator is located in the gantry 6 to generate the high powered radiation required for the therapy. The axis of the radiation bundle emitted from the linear accelerator and the gantry 6 is designated by 10. Electron, photon or any other detectable radiation can be used for the therapy.

During the treatment, the radiation beam is trained on a zone 12 of an object 13, for example, a patient who is to be treated and who lies at the isocenter of the gantry rotation. The rotational axis 8 of the gantry 6, the rotational axis 14 of a treatment table 16, and the beam axis 10 intersect in the isocenter.

The plates or leaves of the beam shielding device within the treatment head 4 are substantially impervious to the emitted radiation. The collimator leaves or plates are mounted between the radiation source and the patient in order to delimit the field. Areas of the body, for example, healthy tissue, are therefore subject to as little radiation as possible and preferably to none at all. The plates or leaves are movable such that the distribution of radiation over the field need not be uniform (one region can be given a higher dose than another). Furthermore, the gantry can be rotated so as to allow different beam angles and radiation distributions without having to move the patient.

The radiation treatment device 2 also includes a central treatment processing or control unit 200 which is typically located apart from the radiation treatment device 2. The radiation treatment device 2 is normally located in a different room to protect the therapist from radiation. The treatment unit 200 includes output devices such as at least one visual display unit or monitor 70 and an input device such as a keyboard 19. Data can be input also through data carriers such as data storage devices or a verification and recording or automatic setup system.

The treatment processing unit 200 is typically operated by the therapist who administers actual delivery of radiation treatment as prescribed by an oncologist by using the keyboard 19 or other input device. The therapist enters into the control unit of the treatment unit 200 the data that defines the radiation dose to be delivered to the patient, for example, according to the prescription of the oncologist. The program can also be input via another input device, such a data storage device. Various data can be displayed before and during the treatment on the screen of the monitor 70.

SYSTEM BLOCK DIAGRAM

Figure 2:
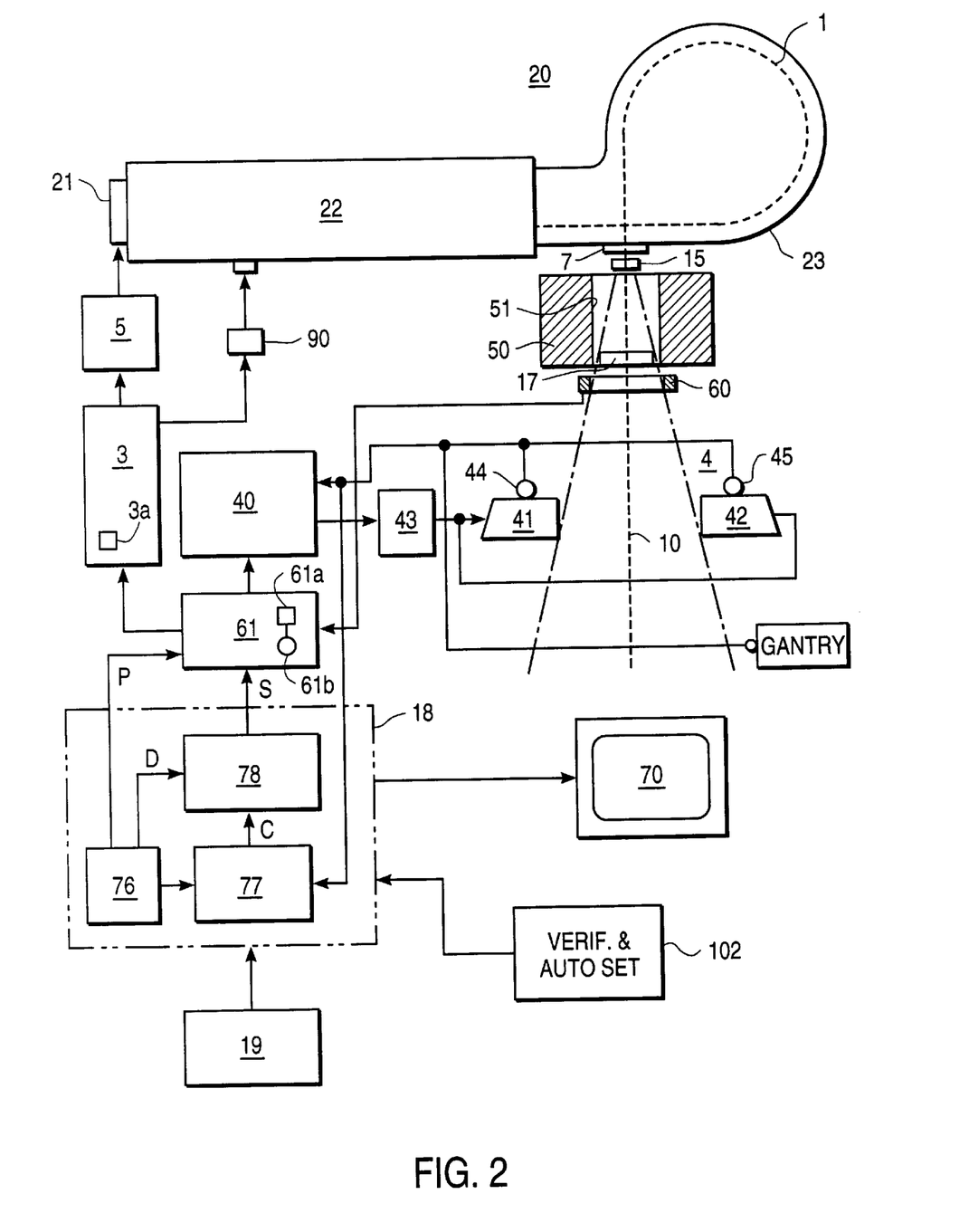
FIG. 2 is a more detailed block diagram illustrating portions of the present invention.

Turning now to FIG. 2, a block diagram of the radiation treatment device 2 and portions of the treatment unit 200 are, according to the present invention, illustrated in greater detail. An electron beam 1 is generated in an electron accelerator 20. The electron accelerator 20 includes an electron gun 21, a wave guide 22 and an evacuated envelope or guide magnet 23. A trigger system 3 generates injector trigger signals and supplies them to the injector 5. Based on these injector trigger signals, the injector 5 generates injector pulses which are fed to the electron gun 21 in the accelerator 20 for generating electron beam 1. The electron beam 1 is accelerated and guided by the wave guide 22. For this purpose, a high frequency source 90, such as a magnetron or klystron, is provided, which supplies radio frequency signals for the generation of an electromagnetic field supplied to the waveguide 22. The electrons injected by the injector 5 and emitted by the electron gun 21 are accelerated by this electromagnetic field in the waveguide 22 and exit at the end opposite to electron gun 21 in electron beam 1.

As will be discussed in greater detail below, the trigger system 3 may include a phase shifter 3a for shifting the RF modulator and the injector 5 in and out of phase. In particular, the phase shifter 3a may be configured to delay the activation of the injector trigger by a predetermined period, such as 2.8 ms, to ensure that the beam is off during a pause condition.

The electron beam 1 enters a guide magnet 23 and from there is guided through a window 7 along axis 10. After passing through a first scattering foil 15, the beam goes through a passageway 51 of a shield block 50 and encounters a flattening filter 17. Next, it is sent through a measuring chamber 60 in which the dose is ascertained. If the scattering foil is replaced by a target, the radiation beam is an X-ray beam; in this case, the flattening filter 17 may be absent, but it is typically present.

Finally, a beam shielding device 401 is provided in the path of radiation beam 1, by which the irradiated field of the subject of investigation is determined. As illustrated, the beam shielding device 401 includes a plurality of opposing plates 41 and 42, only two of which are illustrated for convenience. In one embodiment, additional pairs of plates (not shown) are arranged perpendicular to plates 41 and 42. The plates 41, 42 are moved with respect to axis 10 by a drive unit 43 (which is indicated in FIG. 2 only with respect to plate 41) to change the size of the irradiated field. The drive unit 43 includes an electric motor which is coupled to the plates 41 and 42 and which is controlled by a motor controller 40. Position sensors 44 and 45 are also coupled to the plates 41 and 42, respectively for sensing their positions. As discussed above, the plate arrangement 401 may alternatively or additionally include a multi-leaf collimator having many radiation blocking leaves. The leaves of such a multi-leaf collimator include a plurality of opposing leaf or rod pairs, each driven by a motor or drive unit. The drive units move the leaves in and out of the treatment field, thus creating the desired field shape. The rods, or leaves, are relatively narrow, and cast a shadow of about 0.5 to 1. cm at isocenter.

The motor controller 40 is coupled to a dose unit 61 which may include a dosimetry controller 61a according to the present invention and which is coupled to a central processing unit 18 for providing set values for the radiation beam for achieving given isodose curves. The dosimetry controller 61a according to an aspect of the present invention is configured to monitor for dose rate and accumulated dosage levels during PAUSE conditions. Accordingly, a memory unit 61b are provided, which may store values corresponding to dose rate and accumulated dosage thresholds, as will be discussed in greater detail below. According to the present invention, if the detected dose rate and the dose exceed the thresholds, an interlock is asserted.

In addition, as will be discussed in greater detail below, the memory 61b may be used to store a look-up table of values used to compensate for dosimetric delays during a start-up period. In addition, a timer (not shown) may be provided to determine the start-up period and/or predetermined compensation times during the start-up period.

In operation, the output of the radiation beam is measured by a measuring chamber 60. In response to the deviation between the set values and the actual values, the dose control unit 61 supplies signals to a trigger system 3 which changes in a known manner the pulse repetition frequency so that the deviation between the set values and the actual values of the radiation beam output is minimized. According to an aspect of the invention, when the high voltage modulator is decoupled, the measuring chamber 60 and the dose control unit 61 are configured to remain active and detect levels of applied radiation. If the levels exceed the threshold(s), the dose control unit 61 asserts an interlock, thereby shutting down the machine.

Upon start-up, the dosimetry controller 61a monitors the output of the radiation beam via the measuring chamber 60. The dosimetry controller 61a then accesses the memory 61b which contains, for example, a lookup table of correction factors and applies the correction factors to the dose such that the signals which are applied to the trigger system minimize the predictable dose error resulting from dosimetry delays.

The central processing unit 18 is programmed by the therapist according to the instructions of the oncologist and performs an optimization so that the radiation treatment device carries out the prescribed radiation treatment. The delivery of the radiation treatment is input through a keyboard 19. The central processing unit 18 is further coupled to provide set signals to the dose control unit 61 that generates the desired values of radiation for controlling trigger system 3. The trigger system 3 then adapts the pulse radiation frequency and other parameters in a corresponding, conventional manner. The central processing unit 18 further includes a control unit 76 which controls execution of the program and the opening and closing of the collimator plates 41, 42 to deliver radiation according to a desired intensity profile.

The central processing unit 18 is configured to deliver auto-sequencing of intensity modulated treatments. One or more functional units, such as a verification and auto setup unit 102 provide inputs to the CPU 18 for controlling the radiation treatment. For example, once the verification and auto set-up unit 102 has verified system set-up, a RAD ON enable signal may be provided to the CPU 18. In response, the CPU 18 may issue a RAD ON signal to the trigger system 3 via the dose unit 61. The trigger system then provides the injector and modulator triggers to the injector and modulator, respectively, to generate the applied radiation beam.

According to the present invention, the central processing unit 18 is configured to automatically deliver predetermined sequences of treatment fields, each field in the sequence being referred to as a segment. In order to do so, the treatment beam must be cycled on and off quickly, and stray doses prevented. The present invention provides this capability by ensuring a rapid stabilization sequence for the high voltage and RF power systems prior to BEAM ON.

PRECISION BEAM CONTROL

Figure 3:
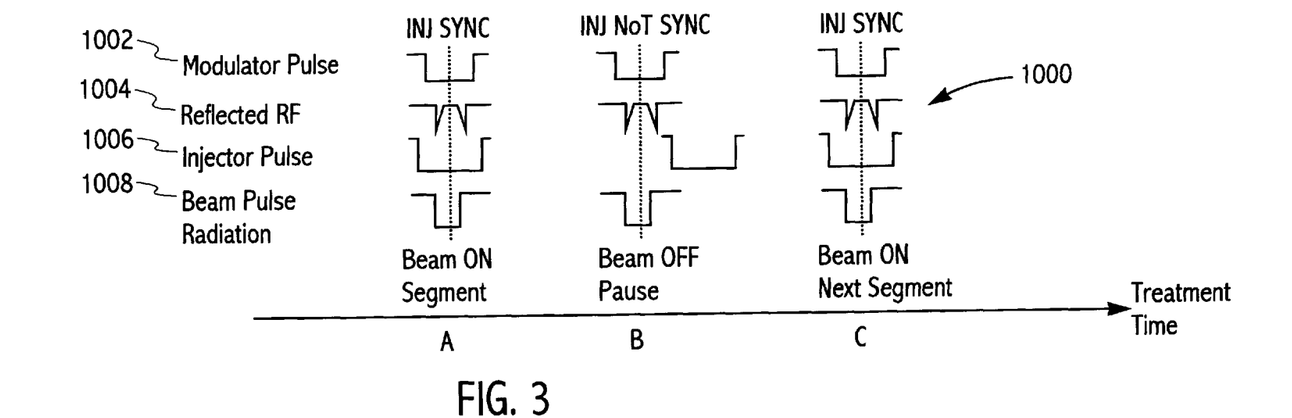
FIG. 3 is a diagram of an exemplary pulse sequence.

Turning now to FIG. 3, a diagram 1000 illustrating the techniques of the present invention is shown. in particular, sequences of RF modulator pulses 1002, reflected RF pulses 1004, injector pulses 1006, and beam pulse 1008 are illustrated. During time A, a BEAM ON segment is shown, with the injector pulse 1006 and the modulator pulse 1002 synchronized. Time A is representative of, for example, the delivery of a radiation treatment field. During time B, a BEAM OFF or pause condition is shown. Time B is the period between delivery of segments during the intensity modulated radiation treatment. During this period, various parameters of the delivery may be changed in the auto-sequence. For example, the collimator leaf positions or gantry angle may be adjusted. During time B, the injector pulse 1006 and the modulator pulse 1002 are out of synchronization, so as to ensure that radiation is not applied to the patient. To do so, a predetermined delay may be inserted into the injector pulse sequence to ensure that the injector pulse 1006 lags the modulator pulse 1002. For example, as will be discussed in greater detail below, the injector trigger may be delayed relative to the modulator trigger by 2.8 milliseconds. Finally, during time C, the BEAM ON condition is resumed for delivery of the next segment. Accordingly, the injector pulse 1006 is again synchronized with the RF modulator pulse 1002. Thus, the injector trigger delay is removed.

Figure 4:
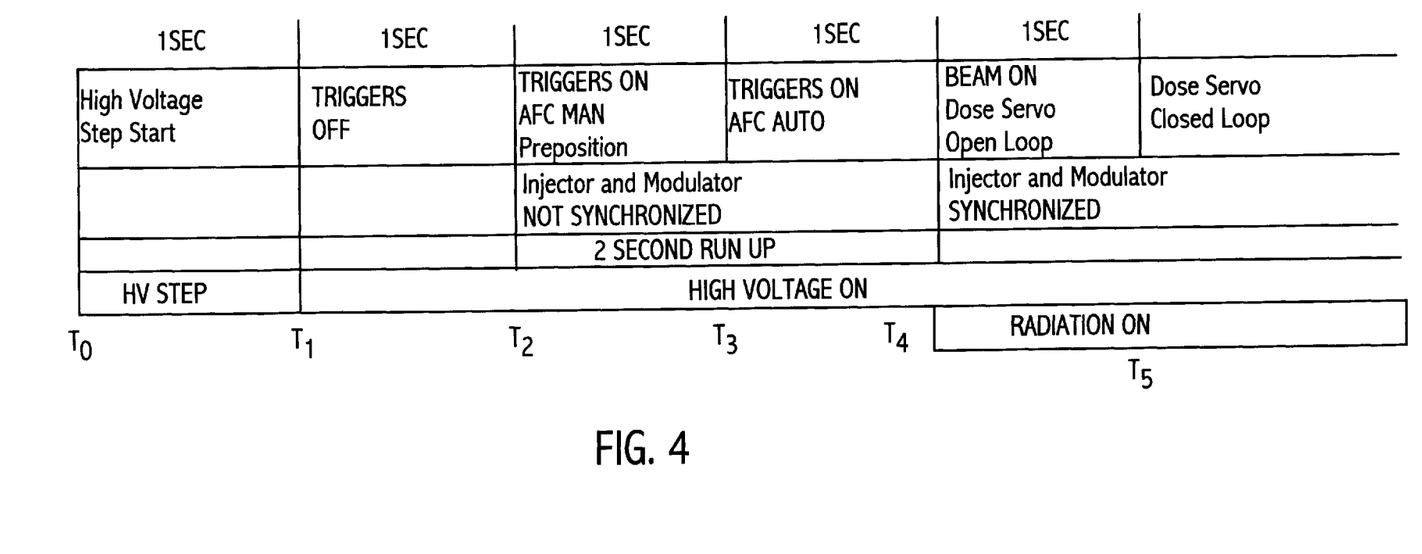
FIG. 4 is a diagram illustrating an initialization sequence according to an embodiment of the invention.

Turning now to FIG. 4, a schematic 400 of the initial stabilization sequence is illustrated. At time $T_0$, power is turned on during the high voltage step. For example, the CPU 18 may respond to a command to start or initialize the system. This initializes the high voltage system. The high voltage step start lasts until time $T_1$, for example, about 1 second. At time $T_1$, the high voltage is on. However, the CPU 18 does not activate the trigger system 3 until time $T_2$. At time $T_2$, the trigger system 3 is activated, for example, by the trigger system 3 receiving the RAD ON signal from the CPU 18. While the triggers are activated, the injector trigger is delayed relative to the modulator pulse. Thus, the injector and modulator are not synchronized. In addition, the auto frequency controls are set to manual. This allows the RF to stabilize and the AFC prepositioning to set the operating frequency within a predetermined bandwidth so that proper AFC servo operation occurs when the AFC is set to auto. At time $T_3$, the triggers are on and the auto-frequency controls are set to automatic. The injector and modulator remain unsynchronized. At time $T_4$, the RAD ON condition is set. The trigger system 3 de-activates the phase shifter 3a such that the injector trigger and the modulator trigger are delivered in synchronization with one another. Consequently, the BEAM ON condition is set, with the dose servo open loop. At time $T_5$, the dose servo is closed loop (The dose servo controls the dose rate, which is a measure of dose delivered per unit time. The dose rate is determined by magnitude of dose per pulse times the dose servo period. The dose rate is controlled by adjusting the pulse repetition frequency of the system. The open loop period allows for sufficient dose servo period to elapse before closing the servo loop). The next pause state is entered into by phase shifting the injector pulse relative to the modulator pulse.

Figure 5:
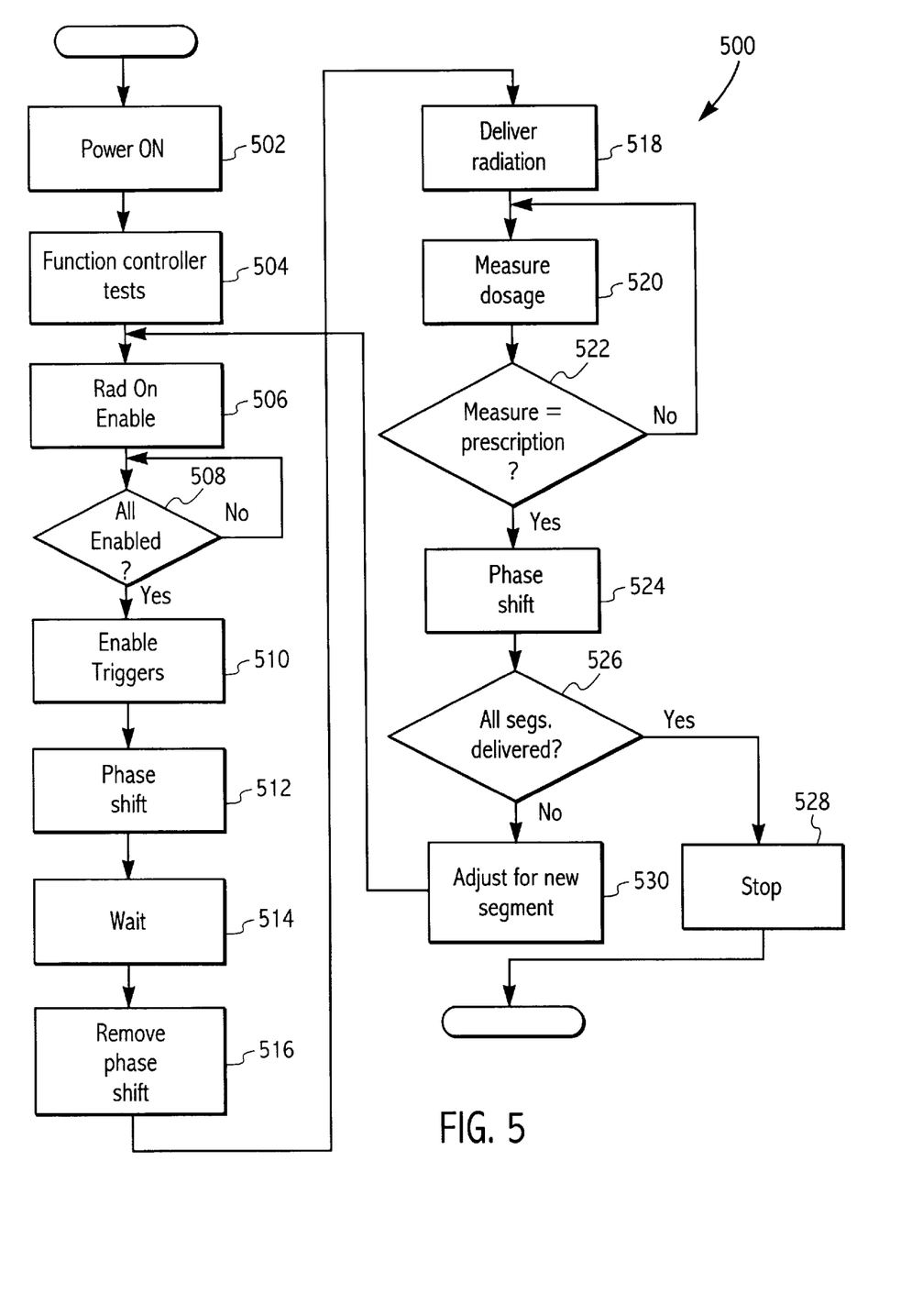
FIG. 5 is a flowchart illustrating operation of a method according to an embodiment of the invention.

Turning now to FIG. 5, a flowchart of system operation is illustrated. In a step 502, power is turned on. At this time, in a step 504, the verification and auto setup unit 102 performs a system test, ensuring, for example, that the collimator leaves are properly positioned for the particular segment. RAD ON Enable commands may be provided to the CPU 18 in a step 506. In a step 508, the CPU 18 determines whether all of the function controllers have provided a RAD ON Enable signal. If not, the CPU 18 waits until all are received. If all the function controllers have provided a RAD ON Enable signal, then the CPU 18 provides a RAD ON signal to the trigger system 3, in a step 510. The trigger system 3 initiates the injector and modulator triggers in a step 512. However, the injector trigger is delayed for 2.8 ms relative to the modulator trigger by activating the phase shifter 3a. This ensures that no radiation is delivered.

After a wait period (step 514), determined for example, by an internal counter, the trigger system 3 deactivates the phase shifter 3a, in a step 516. At this time, radiation is delivered for the treatment segment in a step 518. The dose measurement unit 60 monitors the delivered dosage in a step 520. The measurement information is provided to the dose control unit 61. The dose control unit 61 compares the measured dosage to the prescribed dosage, in a step 522. The monitoring continues while the delivered dosage is less than the prescribed dosage. If the two are determined to be equal, then in a step 524, the trigger system 3 activates the phase shifter 3a, to de-synchronize the modulator and the injector, such that radiation is no longer delivered to the patient.

If all segments have been delivered, as determined in a step 526, then the CPU 18 shuts down the power in a step 528. However, if not all the segments have been delivered, then the modulator and the injector are maintained out of synchronization while the system settings are adjusted for the new segment, in a step 530.

DOSE MONITORING

As discussed above, the radiation therapy device is configured to deliver radiation according to an auto-sequence of intensity modulated field segments. Between field segments, a PAUSE state is entered. In particular, upon entering the PAUSE condition, the verification and auto set up unit 102 receives the previous segment's treatment results from the CPU 18. In addition, the verification and auto set up unit 102 downloads the next field segment to the CPU 18. When the new segment has been received, the CPU 18 automatically moves the jaws 41, 42 and multi-leaf collimator leaves (if required) as well as the gantry and treatment head, if required. In one embodiment, the high voltage may be turned off by the CPU 18 during the PAUSE state. In another embodiment, the injector pulse and the RF modulator pulse are desynchronized; but the high voltage stays on. However, no radiation is delivered.

According to the present invention, the CPU 18 monitors the dose rate and accumulated dose signals at the end of each segment. If the dose controller 61 detects that either the dose rate or the accumulated dosage exceed predetermined thresholds, then an interlock is generated and the system is shut down.

Figure 6:
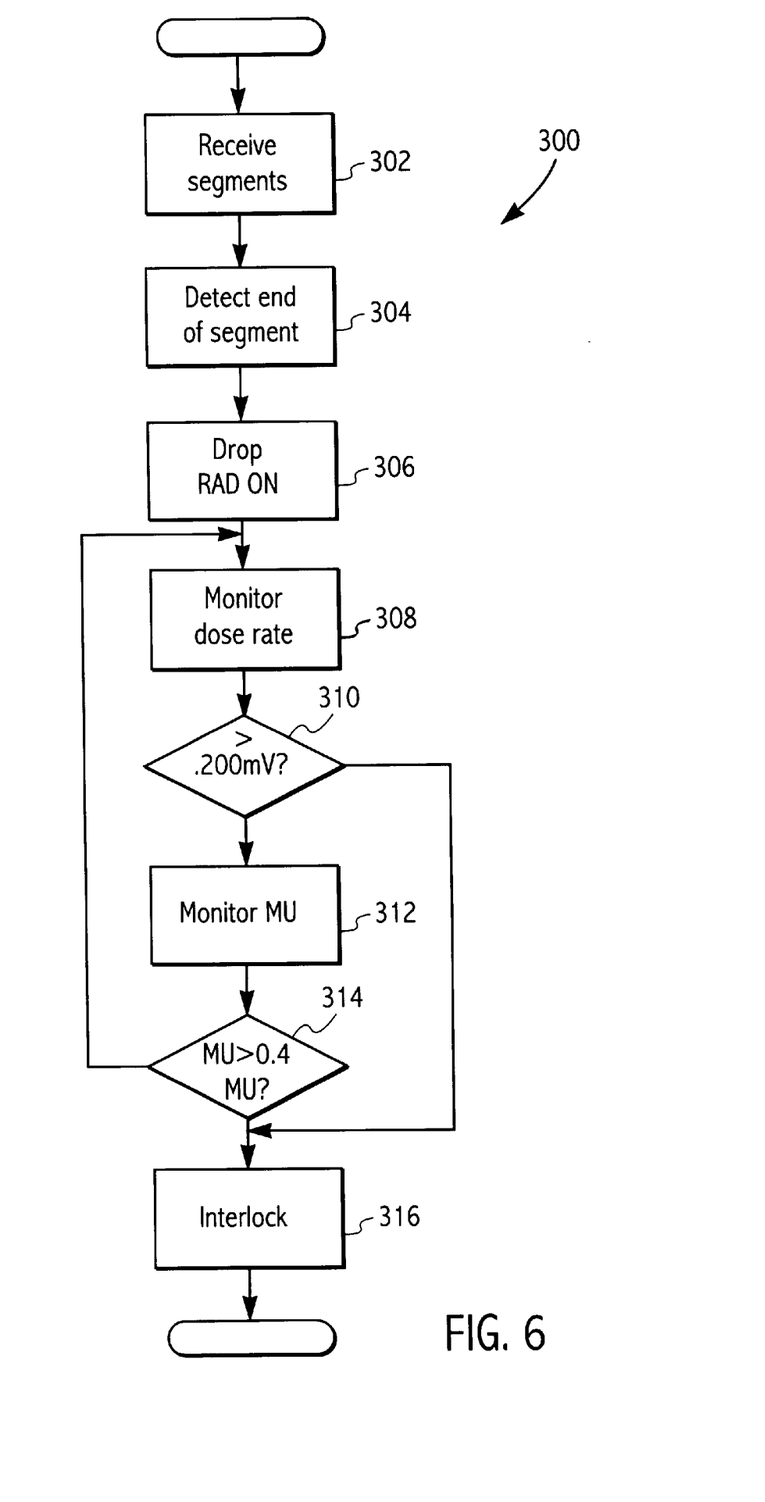
FIG. 6 is a flowchart illustrating a method for dose monitoring according to an aspect of the present invention.

Turning now to FIG. 6, a flow chart 300 illustrating operation of the embodiment of the present invention is shown. In particular, in a step 302, the CPU 18 receives the segment specifications from the verify and auto set up unit 102. Reception of the segment includes reception of an <R> command that indicates that the segment is a non-final segment. In addition, the received segment specification includes threshold values for the dosage rate and accumulated dosage which are stored by the CPU 18 in a memory unit. At the end of the non-final segment, the CPU 18 drops RAD ON but leaves HV ON (high voltage on) enabled until the start of the next segment. In one embodiment, this applies only if the subsequent segment is defined with the same energy, accessories, table position and beam shield position as in the previous segment. In a step 304, the CPU 18 detects the end of the segment. In a step 306, the CPU 18 drops RAD ON and maintains HV ON as enabled in response to the received <R> command. For a final segment, the high voltage is dropped at the completion of the treatment. In a step 308, the CPU continues to monitor the dose rate by receiving inputs from the measurement unit 60 via the dose unit 61. In particular, in one embodiment, at 30 milliseconds after the RAD ON line goes low (with the high voltage on line maintained high), if the dose rate exceeds 200 millivolts (which is proportional to the dose rate), as determined in a step 310, then the CPU 18 asserts an interlock in a step 316. The interlock shuts down the system so that no further radiation is delivered. In addition, in one embodiment 500 milliseconds after the RAD ON line goes low (with the high voltage on line high), the number of monitor units (MU) delivered is measured in a step 312. If the number of monitor units during the PAUSE condition exceeds 0.4 monitor units as determined in a step 314, the CPU 18 will again generate an interlock in a step 316.

PRECISION DOSIMETRY

Figure 7:
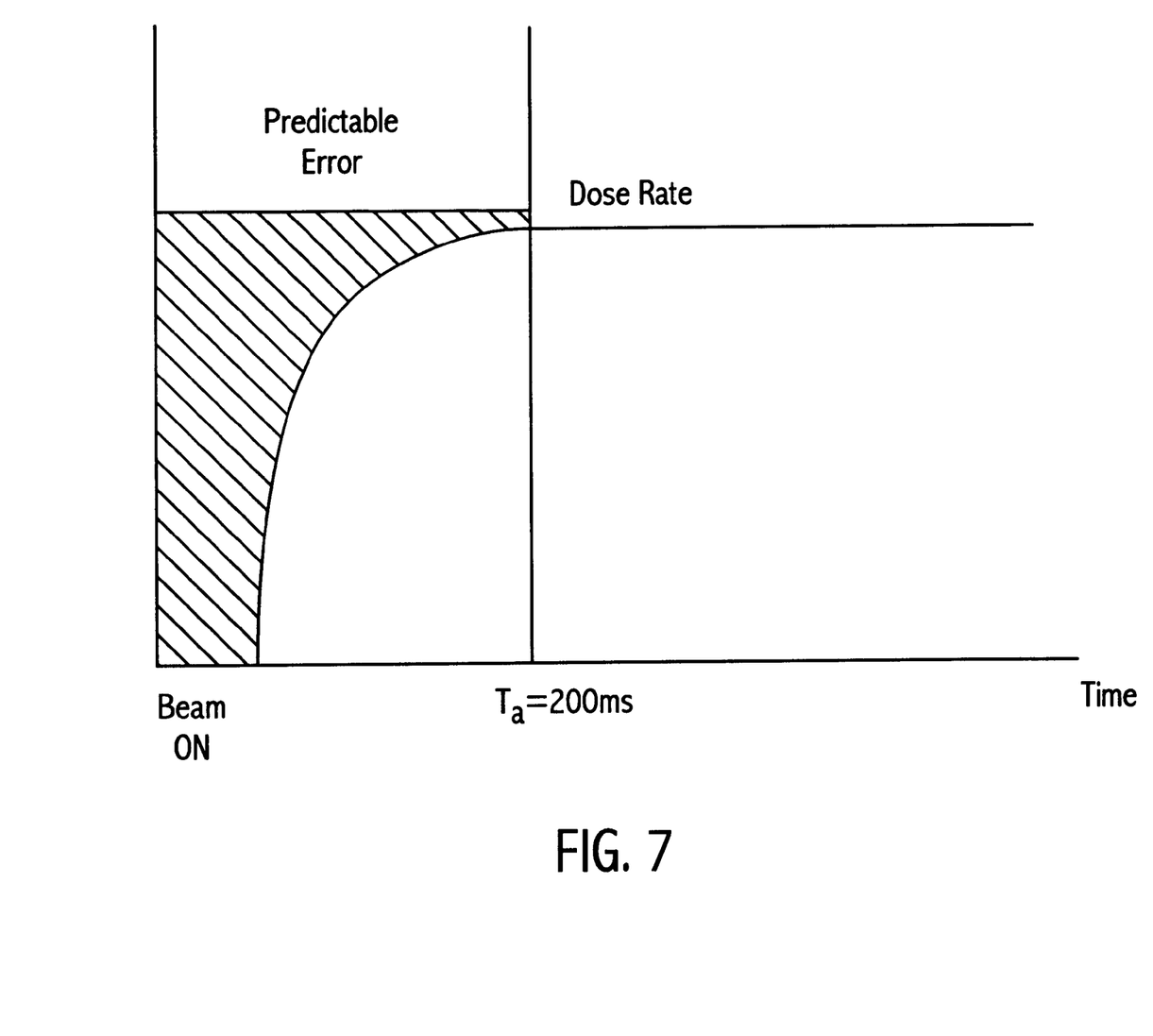
FIG. 7 is a graph of dose rate vs. time.

An important aspect of the invention relates to the initial phase of treatment, after BEAM ON. Referring now to FIG. 7, a diagram illustrating the initial phase of a beam cycle is shown. During the initial phase between BEAM ON and time $T_a$, the dose rate rises to the prescribed dose rate. In one embodiment, the time $T_a$ occurs at approximately 200 milliseconds. During this time, the detected dose rate is known to lag behind the actual dose rate by a known, empirically-derived period. A radiation treatment apparatus according to the present invention compensates for this lag.

Figure 9:
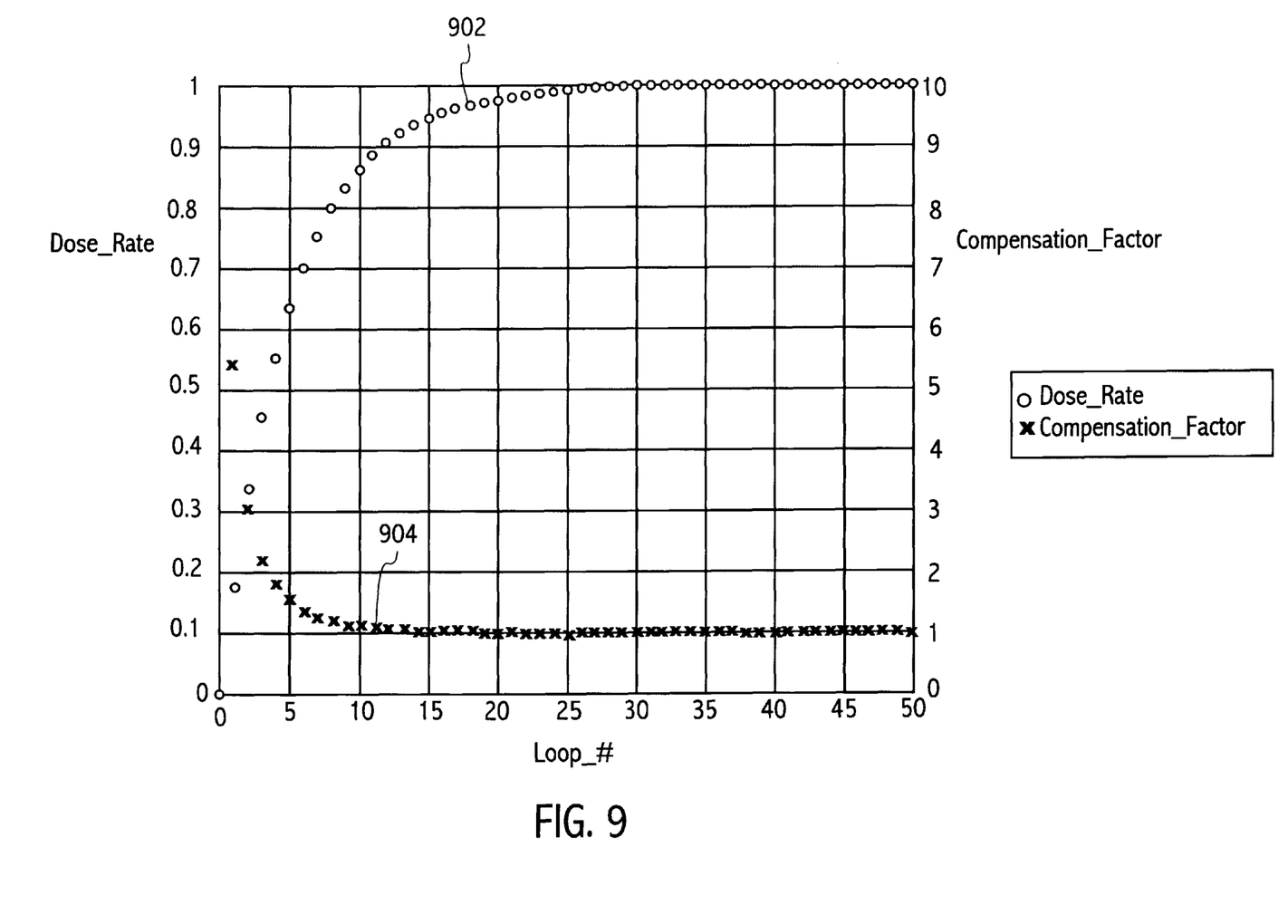
FIG. 9 is a diagram of dose rate and compensation factor vs. loop number according to the present invention.

For example, FIG. 9, is a diagram illustrating the dose rate and loop number and compensation factor. In particular, the horizontal axis shows the loop number, which is representative of elapsed time, as will be discussed in greater detail below. As can be seen, the dose rate represented by a curve 902 increases from zero up to a predetermined level at a loop number equal to 20. A dose rate error occurs between loops zero and 20. Accordingly, a compensation factor, represented by the curve 904, is provided between loop 0 and 20 to overcome the delay from the dosimetry calculations.

Figure 8:
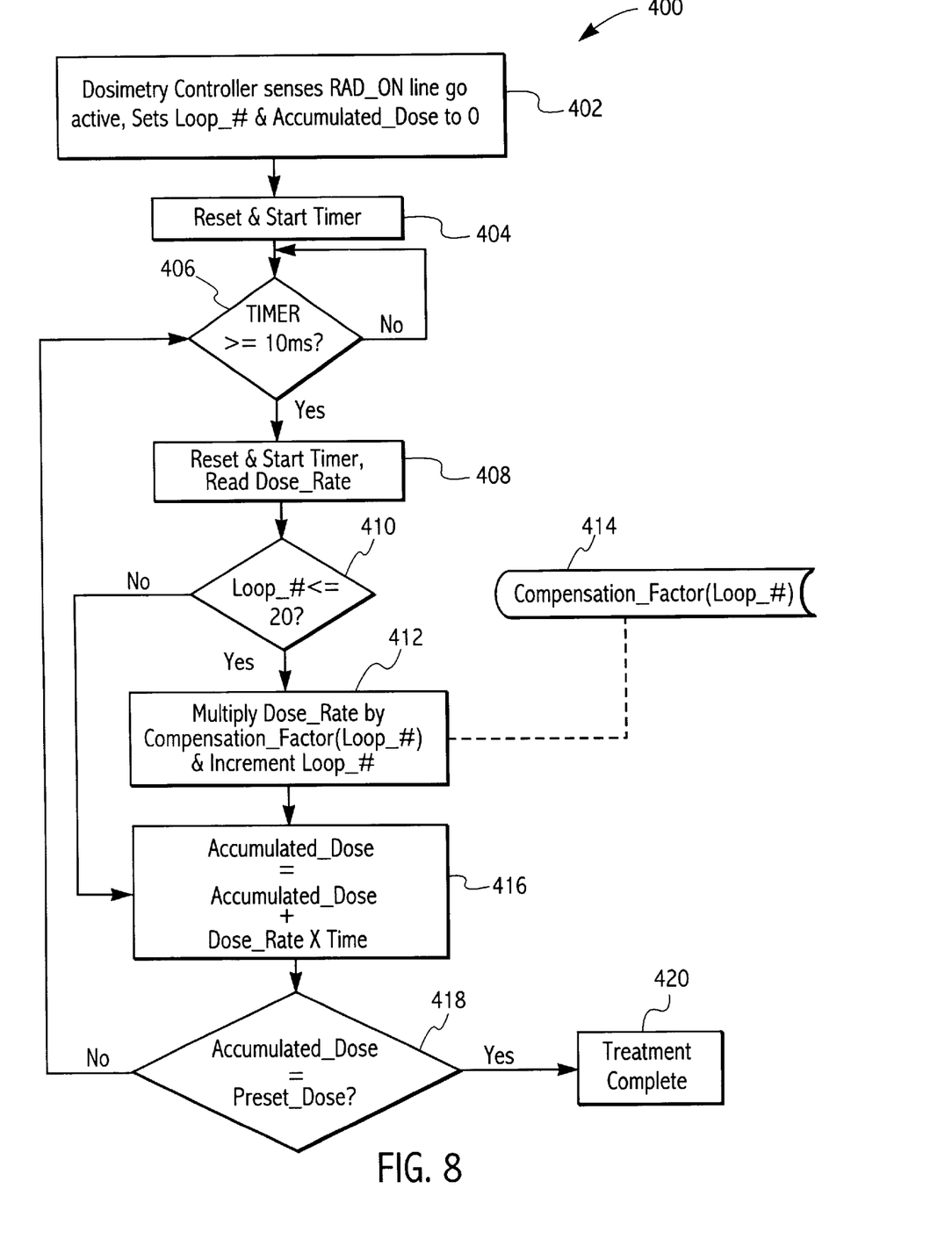
FIG. 8 is a flowchart of a method for precision dosimetry according to an aspect of the invention.

Turning now to FIG. 8, a flowchart illustrating the correction technique according to the present invention is shown. The system samples the dosage periodically during the 200 millisecond startup period and corrects for the amplification delays. In particular, in a step 402, the dosimetry controller 61 senses the RAD ON line going active, sets a loop number and an accumulated dose variable to zero. The loop number in the embodiment illustrated is a number between 1 and 20, with the sampling occurring every ten milliseconds. It is noted that more or fewer loops may be employed. In a step 404, the dosimetry controller 61a resets and starts the timer. In a step 406, it is determined whether the timer is greater than or equal to ten milliseconds. If not, the system recycles. If the timer in step 406 was greater than or equal to ten milliseconds, then in a step 408 the timer is reset and restarted and the dose rate is read by the dosimetry controller 61a via the monitoring chamber 60.

Next, in a step 410, the dosimetry controller 61a determines whether or not the loop number is less than or equal to 20. If so, then in a step 412 the dosimetry controller will multiply the dose rate by the compensation factor which is a function of the loop number and will increment the loop number. As discussed above, the compensation factor 14 is stored in a lookup table 61b and is known through empirical system analysis. For example, dosage measurements may be made from known test systems external to the radiation therapy device. Discrepancies between the dosage determined by the external test device and the radiation treatment apparatus itself are used to establish the correction factors.

If, in step 410, the loop number was not less than or equal to 20, then in a step 416, the accumulated dose is reset to the accumulated dose's previous value plus the dose rate times time. Next, in a step 418, the system determines whether the accumulated dose is equal to the preset dose. If not, then the program cycles back to step 406. However, if the accumulated dose is now equal to the preset dose, then the treatment is completed in a step 420.

As discussed above, in certain instances it is desirable to provide an offset in addition to, or in lieu of, the gain factor compensation at least for small dosages. More particularly, the offset is a predetermined value added to the accumulated dose.

Figure 10:
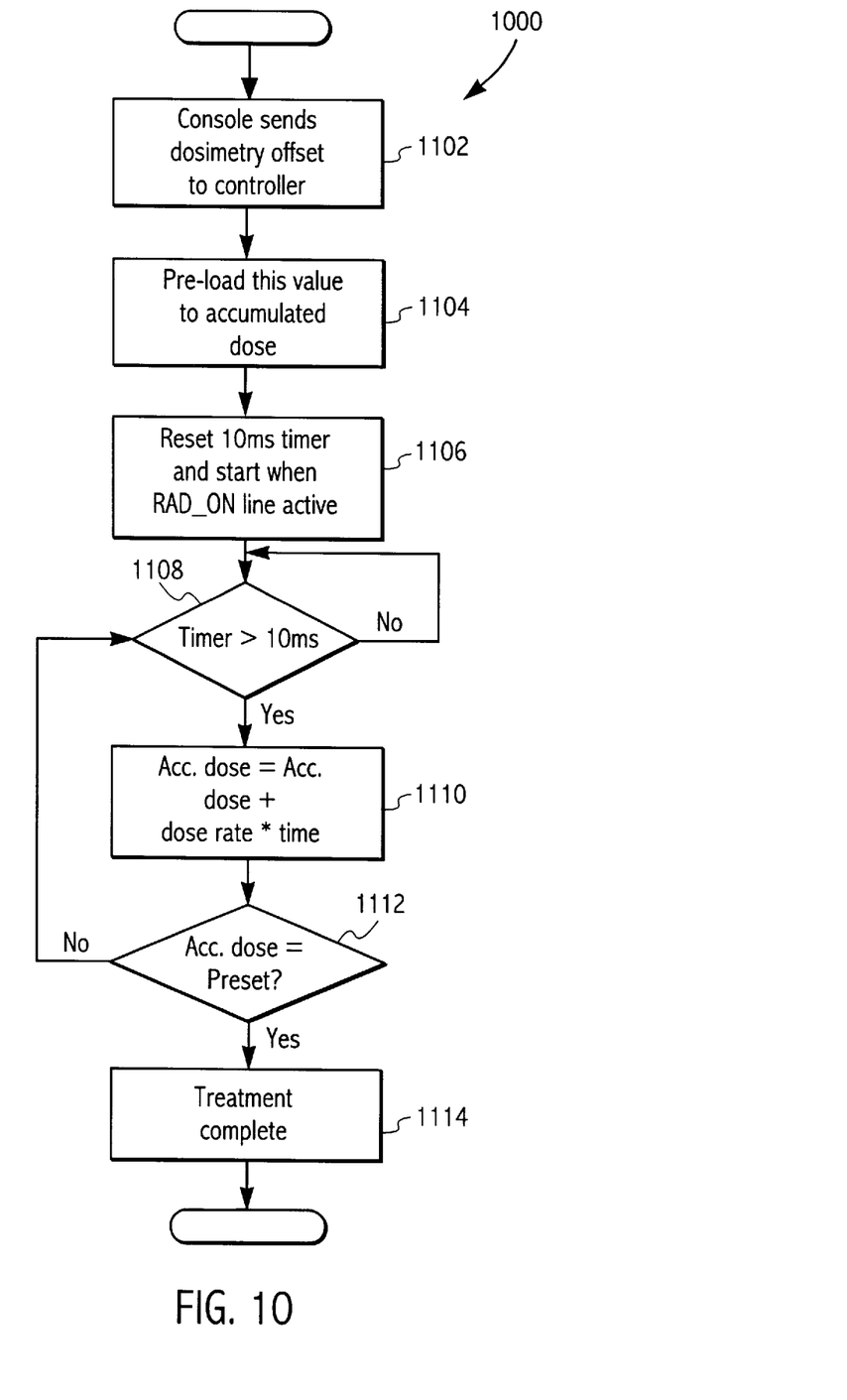
FIG. 10 is a flowchart showing dosimetry offset according to an embodiment of the invention.

Turning now to FIG. 10, a flowchart 1100 is shown of the use of dosimetry offset compensation. In particular, in a step 1102, the console 2 (FIG. 1) sends the predetermined dosimetry offset to the controller. As in the embodiment shown in FIG. 8, the system includes known mechanisms for monitoring accumulated dosages. The accumulated dose value is periodically updated and compared to the prescribed dose. In a step 1104, this dosimetry offset value is pre-added to the accumulated dose value. In a step 1106, the 10 millisecond timer (for example) is reset to zero and started when the RAD ON line is active. In a step 1108, the timer determines whether or not 10 milliseconds have elapsed. If 10 milliseconds have elapsed, then in a step 1110, the accumulated dose is updated to the accumulated dose plus the dose rate over time. If the accumulated dose is equal to the preset or prescribed dose, as determined in a step 1112, then in a step 1114 the treatment is considered to be complete. If, however, the accumulated dose does not equal the preset dose, then the timer is checked again back in step 1108 and the accumulated dose updated in step 1110.

What is claimed is:

1. A method for delivering radiation from a radiation source to a body, comprising:
   (a) providing one or more offset radiation compensation values;
   (b) delivering a predetermined dose of radiation;
   (c) measuring said predetermined radiation dose at predetermined time intervals; and
   (d) compensating said predetermined radiation dose with said one or more radiation offset values as a function of said measured radiation.

2. A method according to claim 1, said compensating comprising compensating during a predetermined period, said predetermined period being before a radiation dose rate has reached a predetermined level.

3. A method according to claim 2, said predetermined period being about 10 milliseconds from RAD ON.

4. A method according to claim 1, said delivering comprising delivering said radiation dose as part of an intensity modulated radiation treatment.

5. A method according to claim 4, said delivering comprising delivering said intensity modulated radiation treatment as an auto-sequenced treatment.

6. A system for delivering radiation from a radiation source to a body, comprising:
   means for providing one or more offset radiation compensation values;
   means for delivering a predetermined dose of radiation;
   means for measuring said predetermined radiation dose at predetermined time intervals; and
   means for compensating said predetermined radiation dose with said one or more radiation offset values as a function of said measured radiation.

7. A system according to claim 6, said compensating means including means for multiplying said radiation compensation values with a dose rate to adjust said predetermined radiation dose.

8. A system according to claim 7, said compensating means comprising means for compensating during a predetermined period, said predetermined period being before a radiation dose rate has reached a predetermined level.

9. A system according to claim 6, said delivering means comprising means for delivering said radiation dose as part of an intensity modulated radiation treatment.

10. A system according to claim 9, said delivering means comprising means for delivering said intensity modulated radiation treatment as an auto-sequenced treatment.

11. A system for delivering radiation from a radiation source to a body, comprising:
    a linear accelerator adapted to deliver a predetermined dose of radiation;
    a memory adapted to store one or more offset radiation compensation values;
    a dosimetry controller adapted to measure said predetermined radiation dose at predetermined time intervals; and
    wherein said dosimetry controller is adapted to compensate said predetermined radiation dose responsive to said measured radiation dose using said one or more radiation offset values.

12. A system according to claim 11, said dosimetry controller adapted to compensate during a predetermined period, said predetermined period being before a radiation dose rate has reached a predetermined level.

13. A system according to claim 11, said linear accelerator adapted to deliver said radiation dose as part of an intensity modulated radiation treatment.

14. A system according to claim 13, said linear accelerator adapted to deliver said intensity modulated radiation treatment as an auto-sequenced treatment.

15. A controller for a radiation therapy device, said controller adapted to store one or more radiation compensation values and compensate a detected predetermined radiation dose responsive to a measured radiation dose value using said radiation compensation values.

16. A controller according to claim 15, said radiation compensation values comprising one or more gain factors.

17. A controller according to claim 15, said radiation compensation values comprising one ore more offset values.

* * * * *